United States Patent [19]

Kobori et al.

[11] Patent Number: 4,650,885
[45] Date of Patent: Mar. 17, 1987

[54] PROCESS FOR PREPARING DERIVATIVES OF NAPHTHAZARIN

[75] Inventors: Yoshihiro Kobori, Kamakura; Tetsuya Takezono, Yokohama, both of Japan

[73] Assignee: Nippon Oil Co., Ltd., Tokyo, Japan

[21] Appl. No.: 857,357

[22] Filed: Apr. 30, 1986

[30] Foreign Application Priority Data

May 1, 1985 [JP] Japan .................................. 60-92295
Oct. 31, 1985 [JP] Japan ................................. 60-242658

[51] Int. Cl.$^4$ .......................................... C07D 307/12
[52] U.S. Cl. ...................................... 549/498; 549/472
[58] Field of Search .............................. 549/472, 498

[56] References Cited
PUBLICATIONS

Chem. Pharm. Bull., vol. 29 (1981) pp. 116–122.

Primary Examiner—Richard L. Raymond
Attorney, Agent, or Firm—Keil & Weinkauf

[57] ABSTRACT

A process is provided for preparing a derivative of naphthazarin represented by the general formula (I) of:

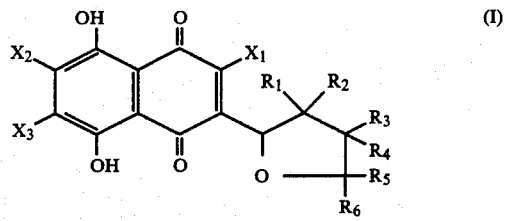

wherein $X_1$, $X_2$ and $X_3$ each stands for an atom or a group consisting of hydrogen, a hydroxyl group, organic residues and halogens; and $R_1$ to $R_6$ each stands for an atom or a group selected from the group consisting of hydrogen and hydrocarbon groups. The derivative of naphthazarin is prepared by the step of reacting, in the presence of an acid catalyst, the following compounds represented by the general formulae (II) and (III):

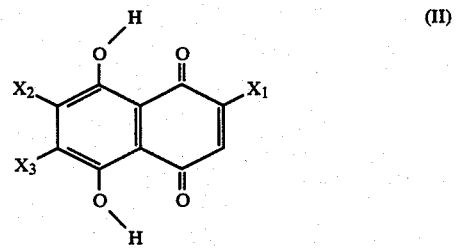

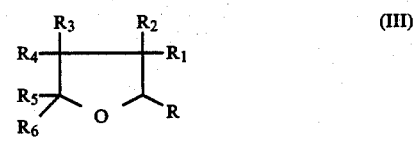

wherein R is an atom or a group selected from the group consisting of hydroxyl, oxyhydrocarbon, siloxy and acyloxy groups and halogen atoms.

17 Claims, No Drawings

PROCESS FOR PREPARING DERIVATIVES OF NAPHTHAZARIN

BACKGROUND OF THE INVENTION

1. Field of the Invention:

The present invention relates to a process for preparing derivatives of naphthazarin which are important materials for dyes and medicines. More particularly, it relates to a process for preparing a derivative of naphthazarin represented by the general formula (I) of:

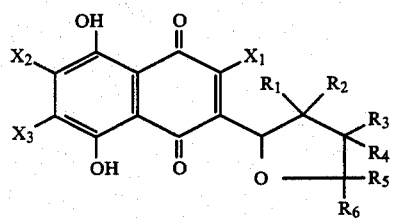

wherein $X_1$ to $X_3$ each stands for an atom or a group selected from the group consisting of hydrogen, a hydroxyl group, organic residues and halogens; and $R_1$ to $R_6$ each stands for an atom or a group selected from the group consisting of hydrogen and hydrocarbon groups.

2. Related Art Statement:

Derivatives of naphthazarin are important materials in the production of dyes and medicines. For example, the R-form isomer of 5,8-dihydroxy-2-(1-hydroxy-4-methyl-3-pentenyl)1,4-naphthalenedione represented by the following structural formula of:

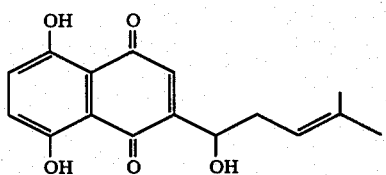

is referred to as Shikonin whereas the S-form isomer thereof is referred to as Alkannin, and both isomers have been used as dyes, medicines and starting materials therefor. On the other hand, the compounds represented by the general formula (I) are important as dyes, medicines and starting materials therefor. Particularly, 5,8-dihydroxy-2-(tetrahydro-5,5-dimethyl-2-furanyl)-1,4-naphthalenedione represented by the following structural formula of:

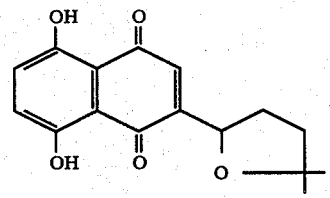

may be prepared by processing the natural Shikonin and Alkannin with an acid catalyst, such as $SnCl_4$, and usually referred to as Cycloshikonin and Cycloalkannin. It has been known in the art that these compounds exert excellent efficacies when used as anti-tumour agents, as reported, for example, by Chem. Pharm. Bull., 29, 116 to 122 (1981). It is also possible to synthesize a material for Shikonin and Alkannin through a method disclosed by the 50th Spring Meeting of the Japanese Chemical Society, preprint, 2R11 and by Japanese Patent Laid-Open Publication No. 175449/1984. However, such a synthesis has not been practised after all, or required very cumbersome processing steps for practical application.

The major reason therefor is that there has not been developed a practically applicable technology for introducing a substituting group having a carbon chain to the skeletal structure of naphthazarin. The two representative examples of the process for the synthesis of naphthazarin will be described hereinbelow. In the first process, an alkyl-1,5-dinitronaphthalene is treated with fuming sulfuric acid as represented by the following reaction formula of:

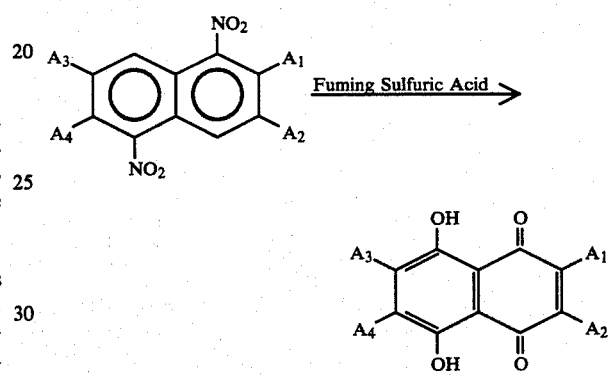

wherein $A_1$ to $A_4$ each stands for hydrogen or an alkyl group.

In the second known process, a derivative of hydroquinone is reacted with a derivative of maleic anhydride through a Friedel-Crafts reaction as represented by the following reaction formula of:

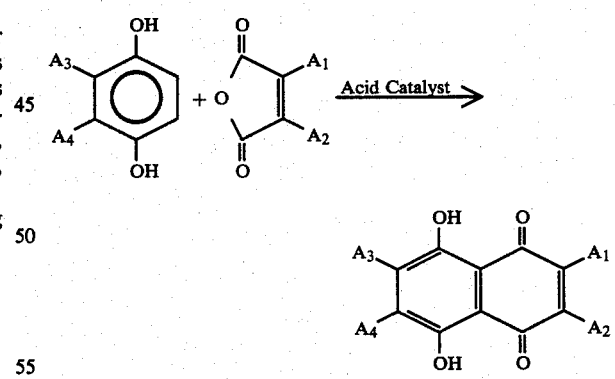

wherein $A_1$ to $A_4$ each stands for hydrogen or an alkyl group.

However, these known processes has been used only in a very narrow application range, because of severe reaction conditions.

On the other hand, Ann. 540, 51 to 71 (1939) discloses a process for preparing derivatives of naphthazarin by reacting naphthazarin with aldehydes in the presence of hydrochloric acid as the catalyst. One example of such process may be represented by the following reaction formula of:

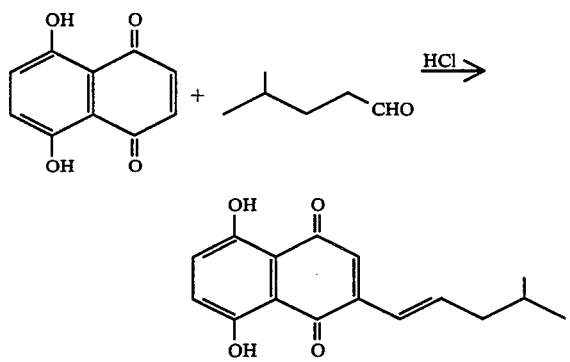

However, a side chain substituting group including oxygen or like elements could not be introduced by the aforementioned prior art process.

Although J. Chem. Res. (S) 1977, 266 to 267 and J. Chem. Soc., Chem. Commun., 1983, 987 to 988 discloses processes for preparing derivatives of naphthazarin by which derivatives of naphthazarin having side chain substituting groups including oxygen are prepared. However, these known processes could not be practically industrialized because of complicated sequential steps with low yield.

Although Shikonin and Alkannin have great utilities, the utilization of these compounds was restricted in quantity, in addition to the problem of high cost, since the resources thereof were limited to natural resources. To overcome these problems, a few processes for preparing the same from starting materials other than natural resources have been developed. For example, J. Chem. Soc., Chem. Commun., 1983, 987 to 988 describes a chemical synthesis of a racemic isomer of Shikonin. However, this known process is not suited for industrialization, since it includes ten and several steps and large quntities of expensive starting materials are required for the practice thereof. It has been also known, for example by Japanese Patent Laid-Open Publication No. 16589/1985, a process for preparing Shikonin by the cultivation of plant cell. However, this process is not satisfactory in consideration of a large expense and low production rate and for the reason that a large expense is needed for the purification of the product.

Accordingly, there is a demand for a process for synthesizing a derivative of naphthazarin, which has substantial efficacy as a medicine of itself and may be used as a starting material for Shikonin and Alkannin, and for synthesizing Cycloshikonin and Cycloalkannin.

OBJECTS AND SUMMARY OF THE INVENTION

A principal object of this invention is to provide a simple process for preparing a derivative of naphthazarin by a single step reation without complicated plural steps.

Another object of this invention is to provide a process for preparing a derivative of naphthazarin in high yield within a short period of time.

The above and other objects of this invention will become apparent from the following detailed description of the invention.

According to the present invention, there is provided a process for preparing a derivative of naphthazarin represented by the general formula (I) of:

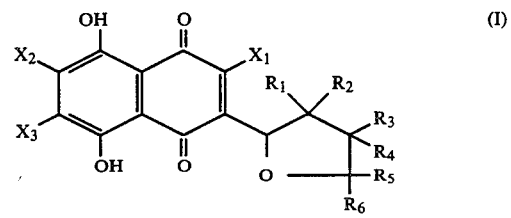

wherein $X_1$, $X_2$ and $X_3$ each stands for an atom or a group selected from the group consisting of hydrogen, a hydroxyl group, organic residues and halogens; and $R_1$ to $R_6$ each stands for an atom or a group selected from the group consisting of hydrogen and hydrocarbon groups;

comprising the step of reacting a first compound represented by the general formula (II) of:

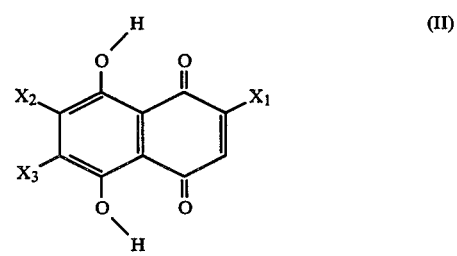

wherein $X_1$, $X_2$ and $X_3$ are the same as defined above; with a second compound represented by the general formula (III) of:

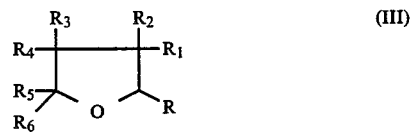

wherein $R_1$ to $R_6$ are the same as defined above and R is an atom or a group selected from the group consisting of hydroxyl, oxyhydrocarbon, siloxy and acyloxy groups and halogen atoms;
in the presence of an acid catalyst.

DESCRIPTION OF THE INVENTION

The derivatives of naphthazarin are characterized by their intramolecular hydrogen bonds. For instance, referring to the compounds represented by the genreral formula (II), they have intramolecular hydrogen bonds represented by the following structural formula of:

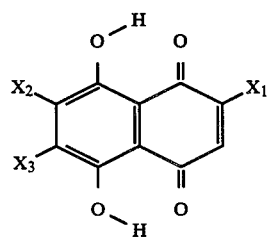

As the result of the presence of such intramolecular hydrogen bonds, they have usually the following resonance structures of:

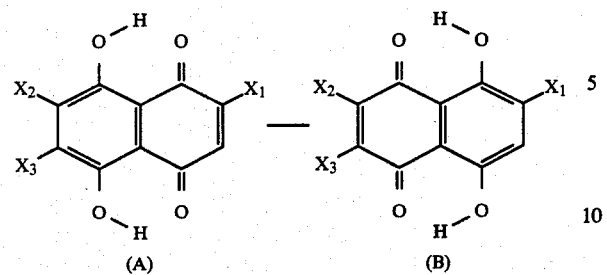

(A) — (B)

It should be clearly understood by a person having ordinary skill in the art that the structural formulae (A) and (B) are different representations of the same compounds. The same is true as to the other derivatives of naphthazarin.

In the first compound used as one of the starting materials in the process of the present invention and represented by the general formula (II), the organic residues included in the substituting groups $X_1$, $X_2$ and $X_3$ are generally selected from organic residues each having 1 to 15 carbon atoms, the examples being hydrocarbon groups such as methyl, ethyl, propyl, isopropyl, cyclohexyl, phenyl and decyl groups; alkoxy groups such as methoxy, ethoxy, propoxy, isopropoxy, cyclohexyloxy and phenoxy groups; amino groups such as methylamino, dimethylamino and phenylamino groups; acyl groups such as formyl and acetyl groups; acyloxy groups such as formyloxy and acetoxy groups; and alkylthio-groups such as methylthio and ethylthio groups.

Structural formulae of specific examples of the first compound (II) which may be used in the present invention will be set forth below. In the following formulae and throughout the subsequent portions of this specification, Me means a methyl group, Et means an ethyl group, Pr means a propyl group and Bu means a butyl group.

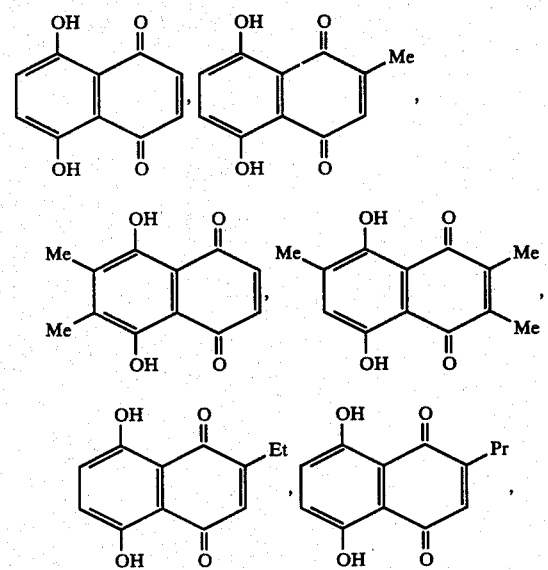

-continued

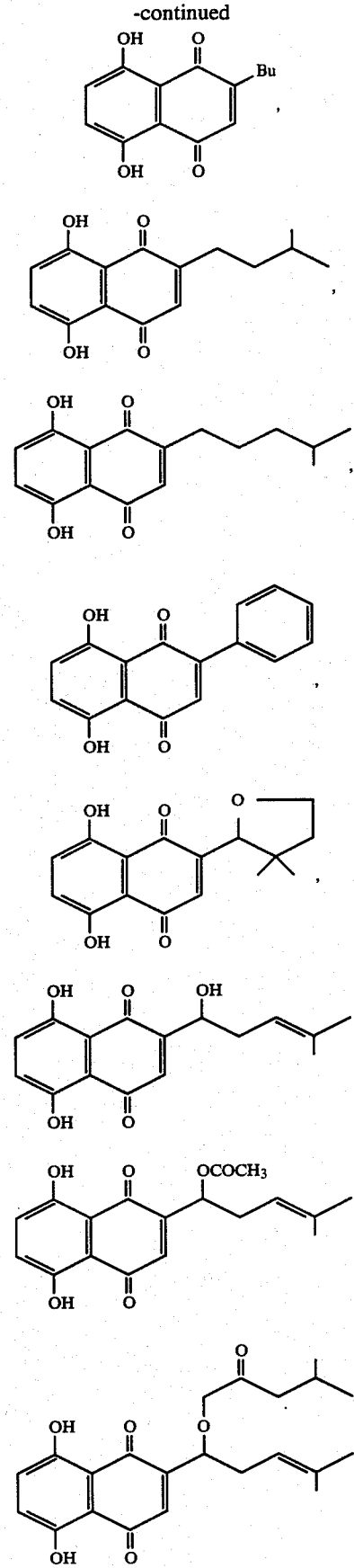

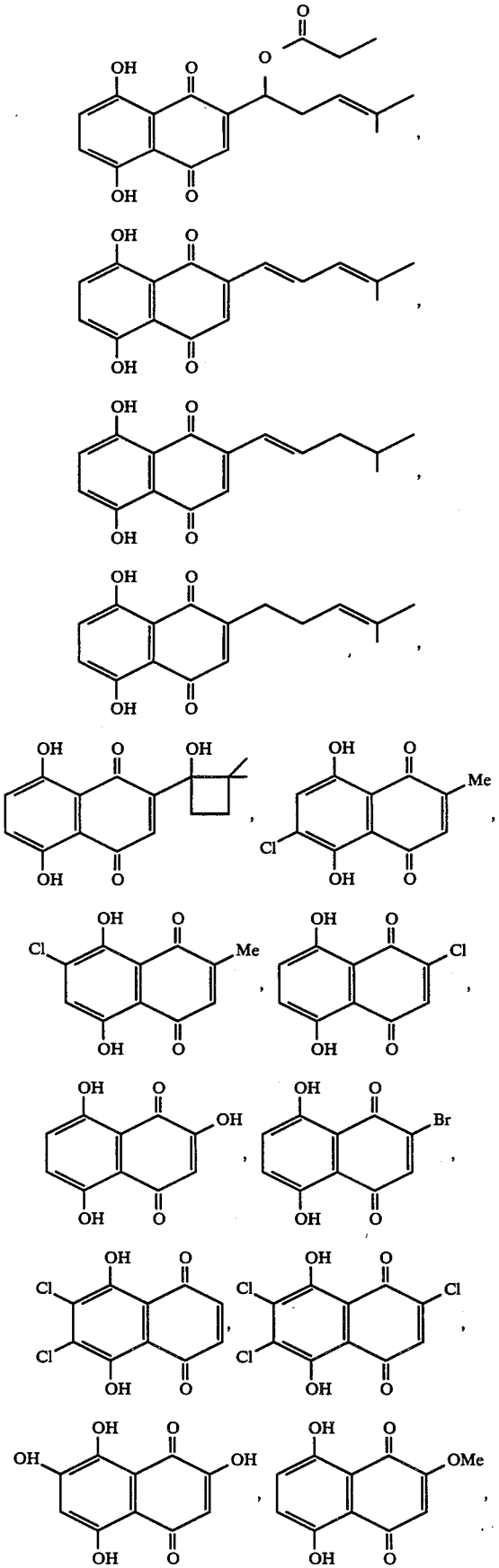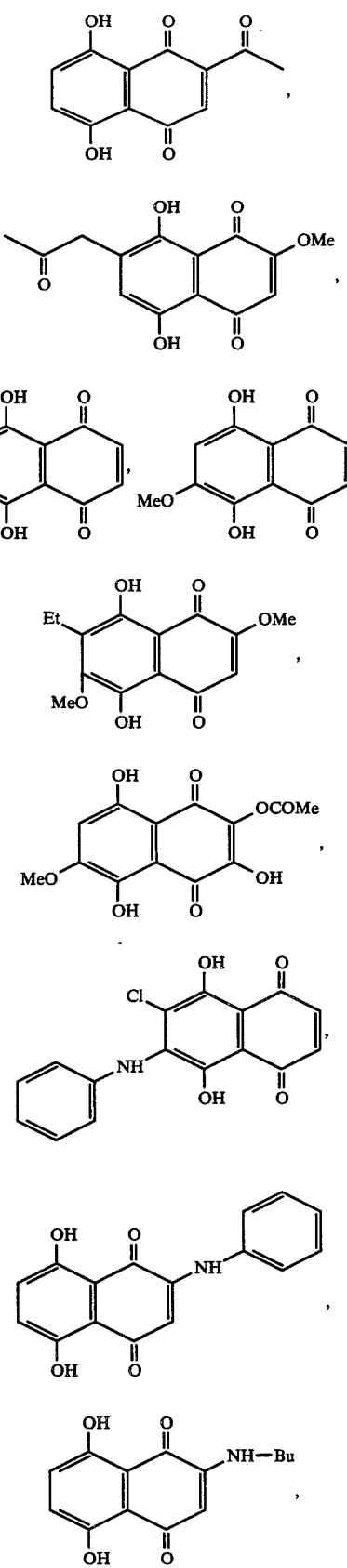

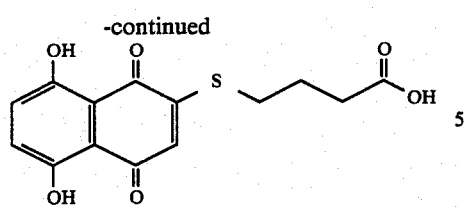

Amongst the compounds set forth above, the most important starting material is 5,8-dihydroxy-1,4-naphthalenedione (commonly referred to as naphthazarin) which may be prepared in good yield, for example, by the nitration of naphthalene to obtain 1,5-dinitronaphthalene which is then treated with fuming sulfuric acid.

In the second compound (III) used as the other starting material in the process of the invention, the hydrocarbon groups indicated by $R_1$ to $R_6$ are generally selected from hydrocarbon groups each having 1 to 15 carbon atoms, the specific examples thereof being methyl, ethyl, propyl, isopropyl, cyclohexyl, phenyl, decyl and naphthyl groups. The oxyhydrocarbon group indicated by R in the structural formula (III) includes alkoxy groups, preferably $C_1$ to $C_{15}$ alkoxy groups, the specific examples being methoxy, ethoxy, propoxy, cyclohexyloxy, phenoxy and naphthoxy groups. The siloxy group indicated by R in the general formula (III) may be a siloxy group substituted by three $C_1$ to $C_{15}$ hydrocarbon groups which may be the same as included in the groups $R_1$ to $R_6$, the specific examples being trimethylsiloxy and diphenylmethylsiloxy groups. Preferable acyloxy groups used as the group R in the general formula (III) are $C_1$ to $C_{15}$ acyloxy groups including sulfoxy, sulfinyloxy and phosphoxy groups other than the carboxy groups, the specific examples being formyloxy, acetyloxy, propionyloxy, cyclohexylcarboxy, benzoyloxy and paratoluylsulfoxy groups.

Accordingly, the specific examples of the compounds represented by the general formula (III) include the following compounds:

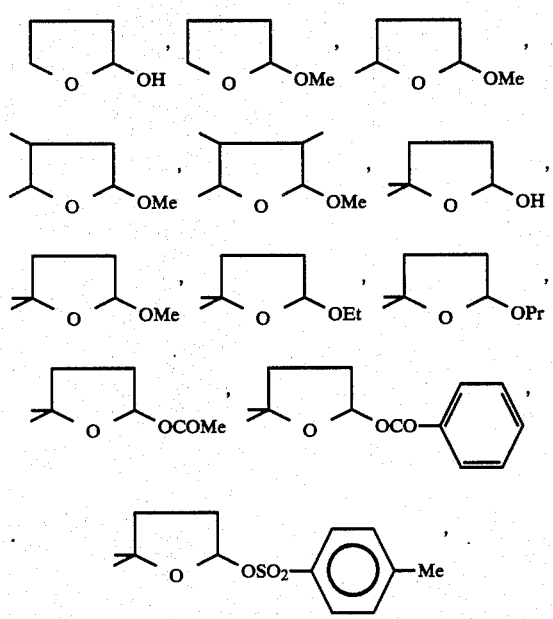

The compounds represented by the general formula (IV) of:

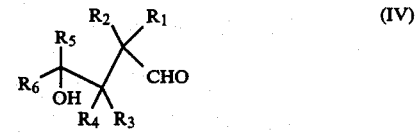

wherein $R_1$ to $R_6$ each stands for an atom or a group selected from the group consisting of hydrogen and hydrocarbon groups; may be converted, under the reaction conditions as defined by the invention, into the compounds represented by the following general formula of:

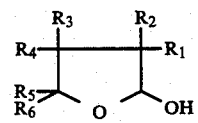

wherein $R_1$ to $R_6$ each stands for an atom or a group selected from the group consisting of hydrogen and hydrocarbon groups.

On the other hand, the compounds represented by the general formula (V) of:

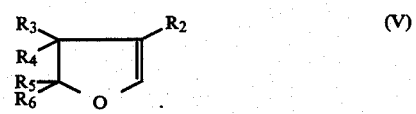

wherein $R_2$ to $R_6$ each stands for an atom or a group selected from the group consisting of hydrogen and hydrocarbon groups; may be converted, by reacting the same with a hydroacid, an alcohol or a silanol under the reaction conditions as defined by the invention, into the compounds represented by the following general formula of:

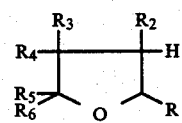

wherein R and $R_2$ to $R_6$ are the same as defined above.

Accordingly, the process of the invention includes the processes wherein the compounds represented by the general formulae (IV) and (V) are used.

Alternatively, the compounds represented by the general formula (III) may be easily prepared by reducing γ-lactones represented by the general formula of:

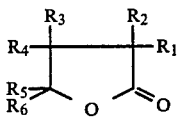

wherein $R_1$ to $R_6$ each stands for an atom or a group selected from the group consisting of hydrogen and hydrocarbon groups; while using diisobutylaluminumhydride or the like reducing agent to prepare hemiacetal isomers thereof followed by etherization, silylation or acylation through a suitable method, as desired. The γ-lactones used as the starting materials in such a process may also be easily prepared, for example by the processes described below. γ-Methyl-γ-valerolactone, which may be used as a starting material for the synthesis of Cycloshikonin and/or Cycloalkannin, may be prepared by using isoprene as the starting material through a simple operation in good yield by the process disclosed in the specification of Japanese Patent Application No. 54219/1985 entitled "Process for the Simultaneous Preparation of Lactone and Carboxylic Acid" filed with the Japanese Patent Office on Mar. 20, 1985 in the name of the assignee same as this application.

As an alternative measure, compounds represented by the formula of:

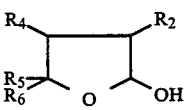

wherein $R_2$ and $R_4$ to $R_6$ each stands for an atom or a group selected from the group consisting of hydrogen and hydrocarbon groups; may be prepared by the hydroformylation of unsaturated alcohols represented by the formula of:

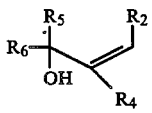

wherein $R_2$ and $R_4$ to $R_6$ each stands for an atom or a group selected from the group consisting of hydrogen and hydrocarbon groups; to synthesize the compounds represented by the following formula of:

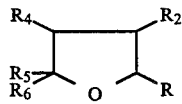

wherein R, $R_2$ and $R_4$ to $R_6$ each stands for an atom or a group selected from the group consisting of hydrogen and hydrocarbon groups; by etherization, silylation or acylation, if necessary.

As a further different method for the preparation of the compounds (III), U.S. Pat. No. 4,123,444 discloses that the following reaction takes place in good yield:

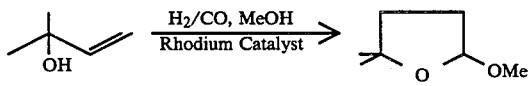

The compounds produced by the reaction set forth above are well suited for the starting materials for the synthesis of Cycloshikonin and Cycloalkannin.

As will be appreciated from the foregoing, the compounds used as the starting materials in the process of the invention may be easily available.

Examples of the acid catalyst used in the process of the invention include hydroacids such as sulfuric acid, phosphoric acid, hydrochloric acid, hydrobromic acid, paratoluenesulfonic acid and trifluoroacetic acid; Lewis acids such as $BF_3$, $BF_3$-etherate, $ZnCl_2$, $SnCl_4$, $AlCl_3$ and silica-alumina; and cation exchange resins such as Amberlite IR-120B (Trade Name) and Dowex HCR (Trade Name). It is desirous that 0.5 to 2 equivalent, preferably 0.8 to 1.5 equivalents, of such an acid be used per unit equivalent of the compound (II).

It is desirous that the 0.05 to 2 mols, preferably 0.1 to 0.8 mol, of the compound (III) be used per mol of the compound (II).

The reaction temperature may be selected depending on the specific substituting groups included in the compounds (II) and (III) and also in consideration of the specific acid catalyst and the solvent used. In general, it is recommended to adopt a temperature in the range of lower than the contact heating, and preferable temperature ranges from—(minus) 20° C. to 150° C., more preferably from 0° C. to 50° C. The reaction speed becomes too low if the reaction temperature is set to an excessively low level.

The reaction time may be properly selected depending on the specific substituting groups included in the starting materials and the specific acid catalyst used, for example, within the range of from 1 minute to 150 hours, preferably from 1 minute to 15 hours, more preferably from 20 minutes to 10 hours.

The process of the invention may be carried out under the solventless condition or in the presence of a solvent. In general, it is convenient to carry out the process in the presence of an orgnic solvent, with the merits that the reaction proceeds smoothly and that the processing after the reaction becomes easier. Examples of solvents used for this purpose include hydrocarbons such as hexane, heptane, octane, benzene, toluene and xylene; alcohols such as methanol, ethanol and propanol; carboxylic acids such as acetic acid, propionic acid and butyric acid; ethers such as diethyl ether, tetrahydrofuran and 1,4-dioxane; lactones such as γ-butylolactone and γ-valerolactone; nitriles such as acetonitrile and benzonitrile; nitro-compounds such as nitromethane and nitrobenzene; esters such as methyl acetate and ethyl acetate; sulfoxides such as dimethyl sulfoxide; amides such as dimethylformamide and dimethylacetoamide; halogenated hydrocarbons such as chloroform, methylene chloride, carbon tetrachloride, dichloroethane, dibromoethane and chlorobenzene; and thio-ethers such as diethyl thioether. A mixture of two or more organic solvents may also be used.

In a preferred embodiment of the present invention, the first compound (II) is initially contacted with any one of the aforementioned acid catalysts prior to reacting the compound (II) with the compound (III), and then the compound (III) is introduced in the reaction system to prepare the compound represented by the general formula (I). By adopting such a two-step process, the reaction speed and the yield in the synthesis of the compound (I) are surprisingly increased.

In the step of contacting the compound (II) with the acid catalyst, the mixture thereof is heated to a temperature of from 50° C. to 150° C., if necessary. The time for heating the mixture of the compound (II) and the acid catalyst is not critical, and ranges generally from one minutes to 3 hours. However, it is not preferred that the mixture is heated at a too high temperature for an excessively long time, since the compound (II) might be affected by such an excessive heating to cause change in its property. Thereafter, the mixture of the compound (II) and the acid catalyst, after having been heated, is reacted with the compound (III).

The process of the invention may be carried out through a batch system or by the use of a continuous reaction system.

The first important feature of the invention resides in that a synthesis of various derivatives of naphthazarin has been developed thereby. In other words, according to the present invention, a variety of derivatives of naphthazarin, which have been synthesized through exceedingly complicated steps or which cannot been sysnthesized by the conventional technology, can be synthesized only through a single step. This provides significant progresses not only from the industrial standpoint of view but also from the standpoint of development of science.

The second important feature of the invention resides in that it provides an epoch-making process for the synthesis of Shikonin or Alkannin which is the most important derivative of naphthazarin. In detail, as has been described hereinbefore, Shikonin and Alkannin may be synthesized 5,8-dihydroxy-2-(tetrahydro-5,5-dimethyl-2-furanyl)-1,4-naphthalenedione which is one of the compounds synthsizable by the process of the invention. Since the products of the process of the invention are racemic modifications or racemic mixtures, it is of course necessary to subject the same to optical resolution in order to obtain Shikonin or Alkannin. However, by the present trend of the development in synthetic technology, such an optical resolution would be realized in due course.

Shikonin is a principal ingredient contained in the extract of lithospermum root and has been widely used as a dye in the Orient for a long time ago. It has been also used as a Chineese medicine for a long time ago as an antifebrile and a toxicide, for example, in the form of an ointment to be applied on a burnt portion. It is set forth in The Pharmacopedia of Japan at the present day and continuously used for a medicine for remedying anal fistula and as Shiunkou. On the other hand, Alkannin is a principal ingredient contained in the extract of alkanna tinctoria tausch predominatly produced in Europe, and has been utilized as a coloring agent for foodstuffs, particularly for coloring wines. In view of the above, it should be recognized that the present invention has opened a route for an economical chemical synthesis of a large quantity of Shikonin and Alkannin which are the compounds of great utility to provide an unfathomable contribution to the dye and pharmaceutical industries.

In addition, it is untterly a novel knowledge to find that the reaction activity of a naphthazarin family compound can be enhanced by the preliminary heating treatment as adopted in a preferred embodiment of the invention, whereby significant industrial and scientific progresses have been offered.

EXAMPLES OF THE INVENTION

Examples of the present invention will now be described for a more detailed understanding of the invention. However, it is noted here that the following Examples should be deemed as illustrative only, and the present invention is not limited only to such examples but defined by the appended claims.

REFERENCE EXAMPLE

Synthesis of Tetrahydro-5,5-dimethyl-2-furanyl Acetate

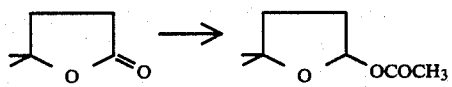

20.2 g (177 millimols) of γ-methyl-γ-valerolactone was dissolved in 80 ml of toluene charged in a 500 ml round bottom flask, and added dropwisely for 1 hour with 100 g of a solution of diisobutylaluminumhydride in toluene (containing 25 g (176 millimols) of diisobutylaluminumhydride) while controlling the temperature of the solution within the range of from—(-minus) 50° C. to—(minus) 60° C. After agitating the admixture or reaction solution at the controlled temerature as described above for 2 hours, the temperature of the reaction solution was raised to 0° C., and then added with a mixture of 100 ml of acetic anhydride and 100 ml of pyridine. Thereafter, 100 ml of acetic acid was added, while carefully maintaining the temperature of the solution below 5° C. against the heat generated from the exothermic reaction, and the mixture was agitated over one night. The resulatant precipitate was filtered, and the filtered precipitate was rinsed sufficiently with a mixed solution of acetic anhydride/pyridine/acetic acid (1:1:1 by volume). The filtrate and the rinsing solution was joined together, and subjected to distillation to obtain 18.2 g (115 millimols, Yield: 65%) of tetrahydro-5,5-dimethyl-2-furanylacetate.

b.p.: 38° C. (2 Torr).

H-NMR(CDCl$_3$, ppm): 1.25 (3H, CH$_3$), 1.40 (3H, CH$_3$), 1.75 to 2.25 (4H, CH$_2$), 2.03 (3H, COCH$_3$), 6.24 (1H, CH).

EXAMPLE 1

Synthesis of 5,8-Dihydroxy-2-(tetrahydro-5,5-dimethyl-2-furanyl)-1,4-naphthalenedione

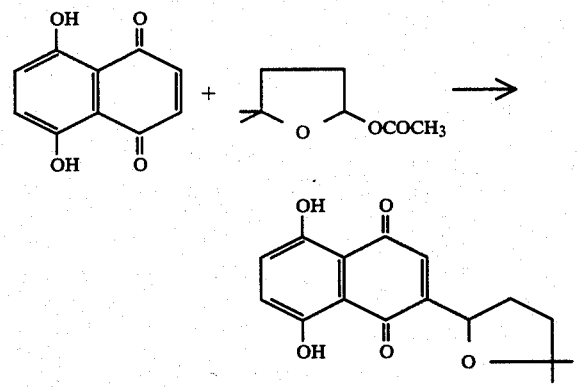

1.01 g (5.31 millimols) of naphthazarin was dissolved in a mixed solvent containing 200 ml of acetic acid and 100 ml of toluene charged in a 500 ml round-bottom flask, and added with 0.66 ml of BF$_3$-etherate. A mixture of 0.421 g (2.66 millimols) of tetrahydro-5,5- dimethyl-2-furanyl acetate and 50 ml of acetic acid was added dropwisely for 7 hours at the room temperature, and then the admixture was agitated for 70 hours. The reaction solution was poured into 500 ml of a saturated saline solution, and extracted with 200 ml of diethyl ether, the extraction with diethyl ether being repeated by two times. The organic phases were joined together and rinsed with 200 ml of a saturated saline solution by two times, and then dried with anhydrous sodium sulfate. After removing the solvent by distillation, the product was purified by means of column chromatography, and then recrystallized in methanol to obtain 0.182 g (0.63 millimols, Yield based on the tetrahydro-5,5-dimethyl-2-furanyl acetate used: 24%) of dark red crystal of 5,8-dihydroxy-2-(tetrahydro-5,5-dimethyl-2-furanyl)-1,4-naphthalenedione.

m.p.: 83° to 86° C.

H-NMR(CDCl$_3$, ppm): 1.36 (3H, CH$_3$), 1.39 (3H, CH$_3$) 1.80 to 2.63 (4H, CH$_2$), 5.15 (1H, CH), 7.19 to 7.22 (3H, ring), 12.52 & 12.53 (2H, OH).

EXAMPLE 2

Synthesis of 5,8-Dihydroxy-2-(tetrahydro-5,5-dimethyl-2-furanyl)-1,4-naphthalenedione

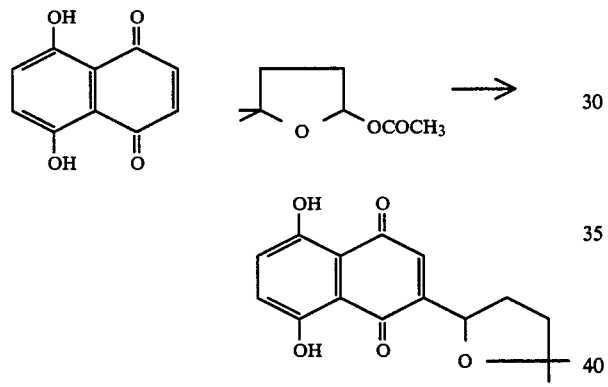

Into a 300 ml round-bottom three-necked falsk provided with a reflux condenser and a dropping funnel, charged were 200 ml of acetic acid, 1.0 g (5.3 millimols) of naphthazarin and 0.66 ml (5.3 millimols) of BF$_3$-etherate. Then the mixed solution in the flask was heated to be refluxed for 40 minutes. After allowed to stand for cooling, the solution was added dropwisely for 10 minutes with a mixed solution containing 0.84 g (5.3 millimols) of tetrahydro-5,5-dimethyl-2-furanyl acetate and 30 ml of acetic acid at the room temperature, while agitating the solution in the flask by a magnetic rotor. After continuing agitation at the room temperature for additional 5 hours, the reaction mixture was poured into ice water. The product was extracted with 200 ml of chloroform by two times, and the extracted organic phase was rinsed with a saturated saline solution and then dried with anhydrous Na$_2$SO$_4$. After removing the solvent by distillation, the product was purified by column chromatography, and then recrystallized in methanol to obtain 0.85 g (2.9 millimols, Yield: 56%) of dark red crystal of 5,8-dihydroxy-2-(tetrahydro-5,5-dimethyl-2-furanyl)-1,4-naphthalenedione.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A process for preparing a derivative of naphthazarin represented by the general formula (I) of:

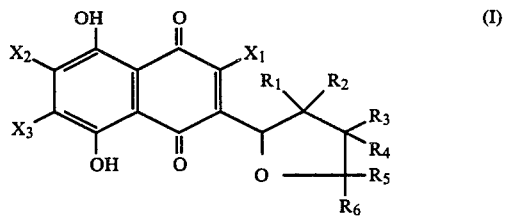

wherein X$_1$, X$_2$ and X$_3$ each stands for an atom or a group selected from the group consisting of hydrogen, a hydroxyl group, organic residues and halogens; and R$_1$ to R$_6$ each stands for an atom or a group selected from the group consisting of hydrogen and hydrocarbon groups;

comprising the step of reacting a first compound represented by the general formula (II) of:

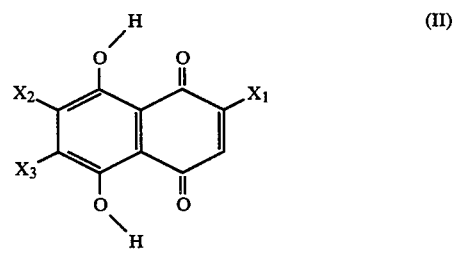

wherein X$_1$, X$_2$ and X$_3$ are the same as defined above; with a second compound represented by the genral formula (III) of:

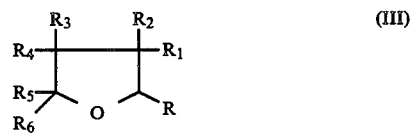

wherein R$_1$ to R$_6$ are the same as defined above and R is an atom or a group selected from the group consisting of hydroxyl, oxyhydrocarbon, siloxy and acyloxy groups and halogen atoms;

in the presence of an acid catalyst.

2. The process according to claim 1, wherein said acid catalyst and said first compound represented by the general formula (II) are heated to 50° C. to 150° C. prior to reacting with said second compound represented by the general formula (III).

3. The process according to claim 1, wherein X$_1$, X$_2$ and X$_3$ each stands for an organic residue having 1 to 15 carbon atoms.

4. The process according to claim 3, wherein said organic residue is selected from the group consisting of methyl, ethyl, propyl, isopropyl, cyclohexyl, phenyl, decyl, methoxy, ethoxy, propoxy, isopropoxy, cyclohexyloxy, phenoxy, methylamino, dimethylamino, phenylamino, formyl, acetyl, formyloxy, acetoxy, methylthio and ethylthio groups.

5. The process according to claim 1, wherein each of $R_1$ to $R_6$ is a hydrocarbon group having 1 to 15 carbon atoms.

6. The process according to claim 5, wherein said hydrocarbon group is selected from the group consisting of methyl, ethyl, propyl, isopropyl, cyclohexyl, phenyl, decyl and naphthyl groups.

7. The process according to claim 1, wherein said oxyhydrocarbon group in said general formula (III) is an alkoxy group having 1 to 15 carbon atoms.

8. The process according to claim 7, wherein said alkoxy group is selected from the group consisting of methoxy, ethoxy, propoxy, cyclohexyloxy, phenoxy and naphthoxy groups.

9. The process according to claim 1, wherein R in said general formula (III) is a substituted siloxy group substituted by three hydrocarbon groups each having 1 to 15 carbon atoms.

10. The process according to claim 9, wherein said substituted siloxy group is selected from the group consisting of trimethylsiloxy group and diphenylmethylsiloxy group.

11. The process according to claim 1, wherein R in said general formula (III) is an acyloxy group having 1 to 15 carbon atoms.

12. The process according to claim 11, wherein said acyloxy group is selected from the group consisting of formyloxy, acetyloxy, propionyloxy, cyclohexylcarboxy, benzoyloxy and paratoluylsulfoxy groups.

13. The process according to claim 1, wherein said acid catalyst is slected from the group consisting of sulfuric acid, phosphoric acid, hydrochloric acid, hydrobromic acid, paratoluenesulfonic acid, trifluoroacetic acid, trifluoromethanesulfonic acid, $BF_3$, $BF_3$-etherate, $ZnCl_2$, $SnCl_4$, $AlCl_3$, silica-alumina and cation exchange resins.

14. The process according to claim 1, wherein said acid catalyst is used in an amount of 0.2 to 2 equivalents per unit equivalent of the first compound represented by the general formula (II).

15. The process according to claim 1, wherein said second compound represented by the general formula (III) is used in an amount of 0.05 to 2 mols per unit molar equivalent of the first compound represented by the general formula (II).

16. The process according to claim 1, wherein said first compound reperesented by the general formula (II) is reacted with said second compound represented by the general formula (III) at a temperature of from—(-minus) 20° C. to 150° C. for one minute to 150 hours.

17. The process according to claim 2, wherein said acid catalyst and said first compound (II) represented by the general formula (II) are reacted over a time period of from one minute to 3 hours prior to the addition of said second compound.

* * * * *